United States Patent [19]
Moulton et al.

[11] Patent Number: 5,632,410
[45] Date of Patent: May 27, 1997

[54] MEANS OF HANDLING MULTIPLE SENSORS IN A GLUCOSE MONITORING INSTRUMENT SYSTEM

[75] Inventors: Joseph L. Moulton, Mishawaka; Frank W. Wogoman, Granger, both of Ind.

[73] Assignee: Bayer Corporation, Elkhart, Ind.

[21] Appl. No.: 638,971

[22] Filed: Jul. 12, 1996

Related U.S. Application Data

[63] Continuation of Ser. No. 423,324, Apr. 17, 1995, abandoned.

[51] Int. Cl.$^6$ .................................................. G07F 11/00
[52] U.S. Cl. ............................................. 221/79; 221/117
[58] Field of Search ........................... 221/70, 79, 80, 221/81, 76, 197, 268, 270, 272, 25, 26, 30, 32

[56] References Cited

FOREIGN PATENT DOCUMENTS

| 0622119 | 4/1994 | European Pat. Off. . |
|---------|--------|----------------------|
| 0622626 | 4/1994 | European Pat. Off. . |

*Primary Examiner*—Kenneth Noland
*Attorney, Agent, or Firm*—Jerome L. Jeffers

[57] ABSTRACT

A sensor dispensing instrument (20) includes a sensor magazine (26) that contains a plurality of blood glucose sensors (38) disposed in sensor slots (30A-J). Each of the sensor slots (30A-J) is in fluid communication with a desiccant cavity (50A-J) in which desiccant material is disposed. The front and rear walls (34, 32) of the sensor magazine (26) are sealed with burst foils (40, 42) so as to seal the sensor slots (30A-J) and the desiccant cavities (36A-J). The sensor instrument (20) has an outer housing (22) with a laterally extending magazine opening (24) adapted to receive the sensor magazine (26). A pivot rod (28) is moved through the magazine (26) and is locked into an operating position. The magazine (26) is rotated on the pivot rod (28) until a detent arm (48) on the instrument housing (22) engages a detent groove (50A-J) on the magazine (26) to position the magazine (26) in a sensor feeding position. Once so positioned, a sensor push rod (54) is pushed forward resulting in the push rod (54) piercing the rear burst foil (42) and engaging a sensor (38) in one of the sensor slots (30A-J) to thereby push the sensor (38) out through the front burst foil (40) and into a testing position. While in this testing position, the sensor (38) can be placed in a blood sample that needs to be analyzed. Once the test is completed, the push rod (54) is advanced forward further to thereby eject the used sensor (38) from the sensor handling instrument (20). The push rod (54) then is retracted to a standby position and the sensor magazine (26) is rotated until the detent arm (48) engages another detent groove (50A-J) so that another sensor slot (30A-J) is in alignment with the push rod (54).

23 Claims, 3 Drawing Sheets

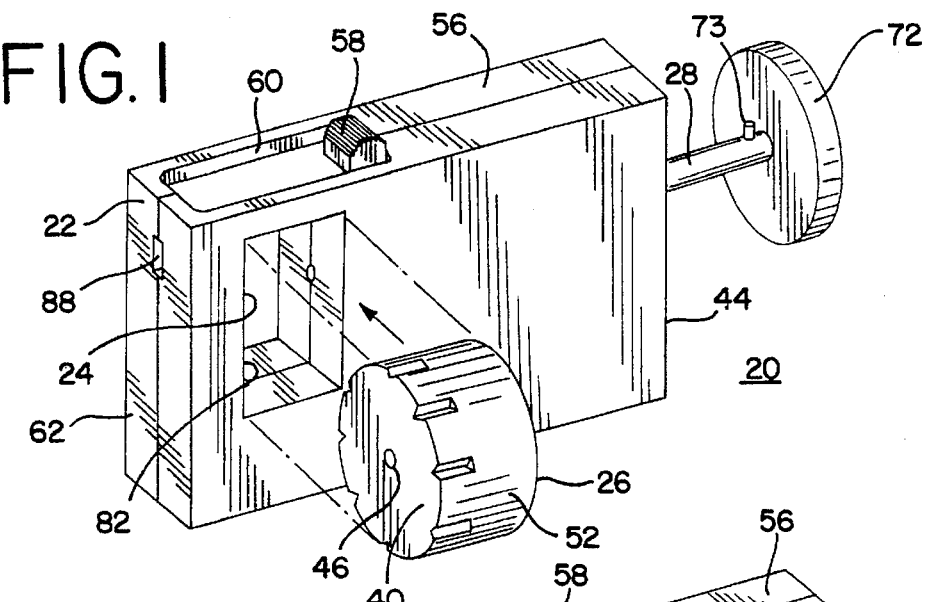
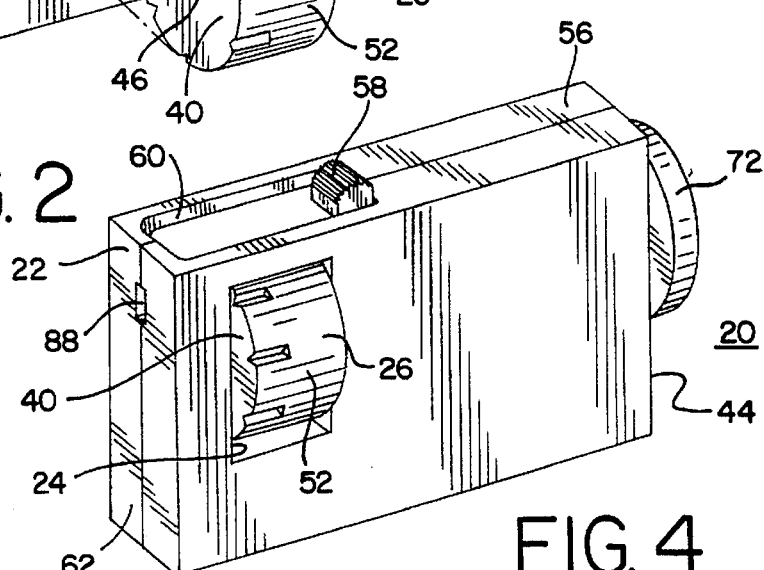
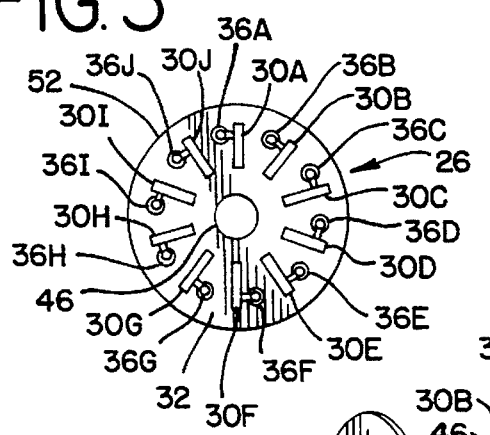
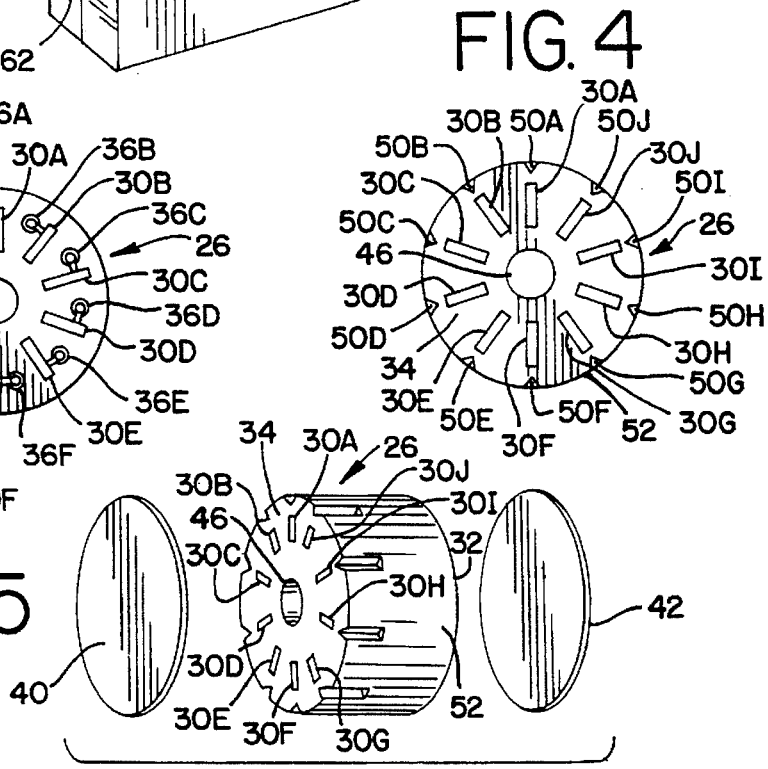

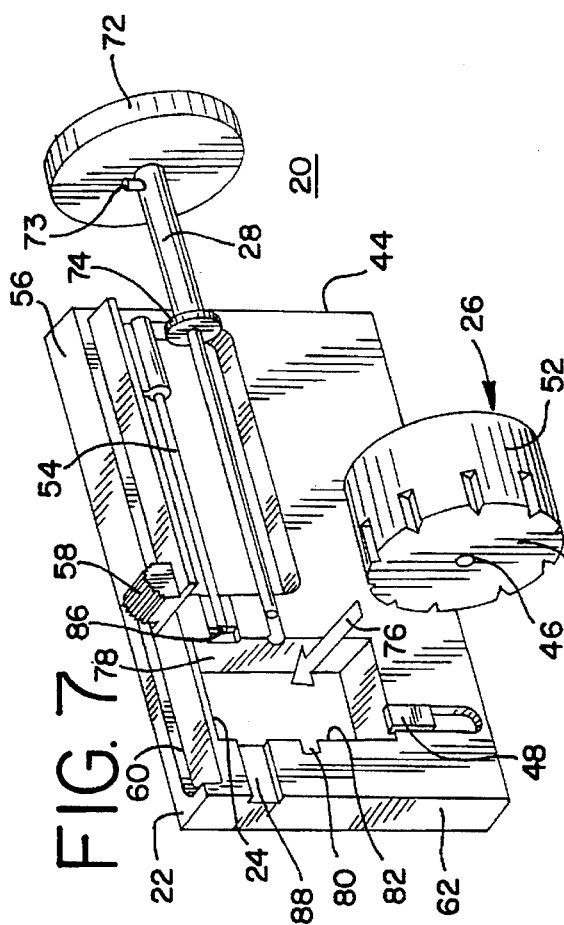
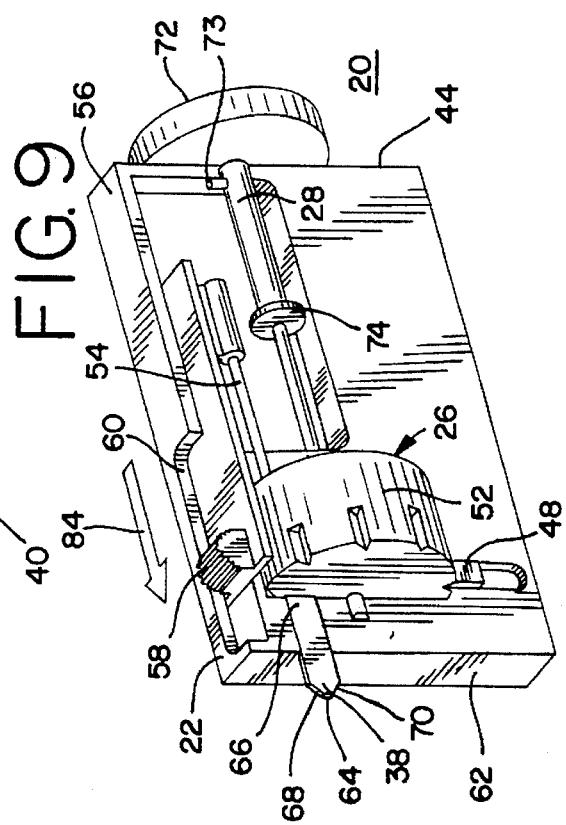
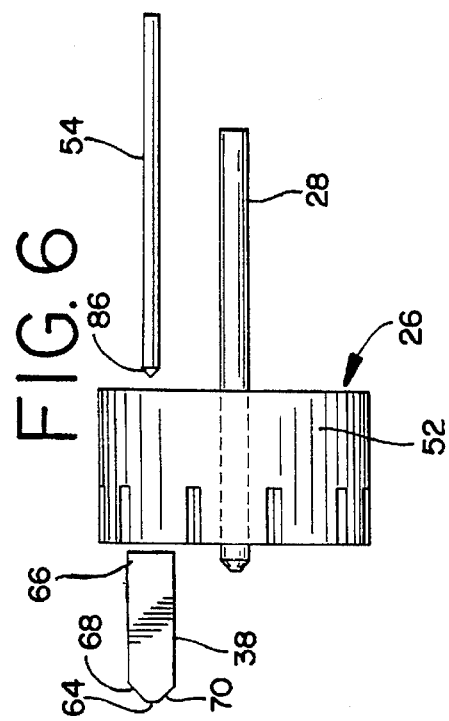
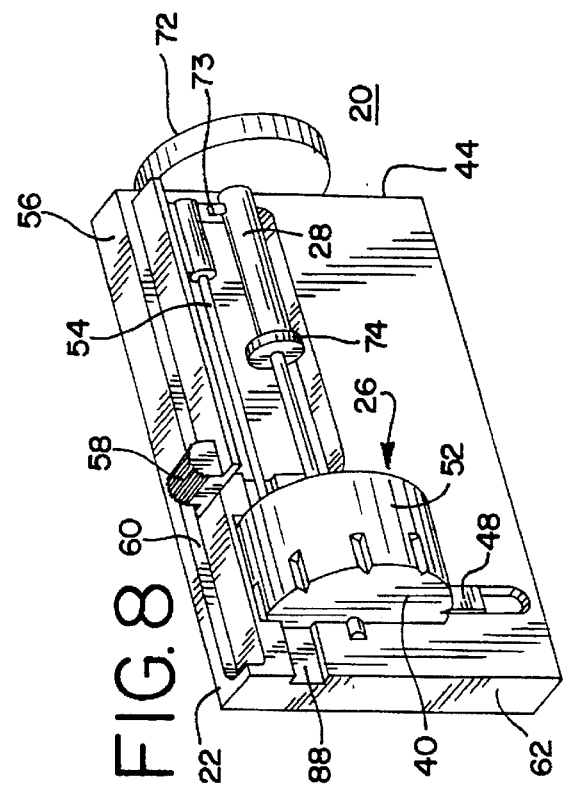

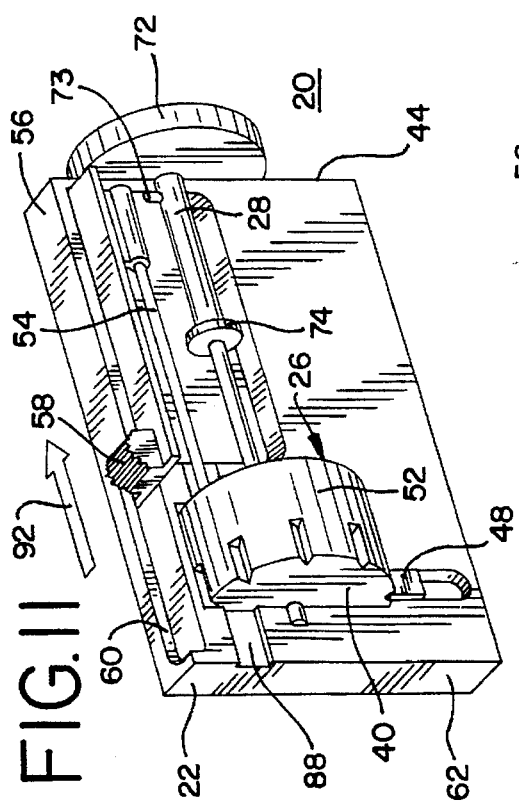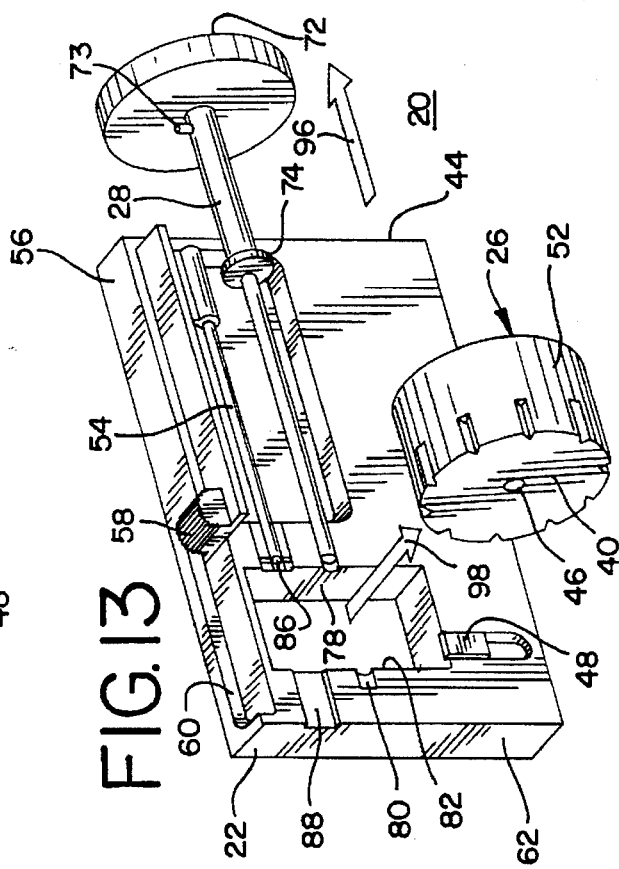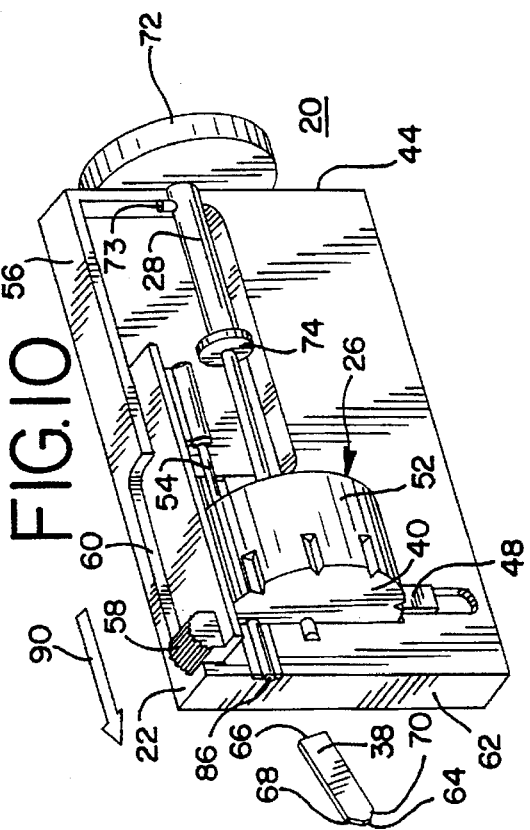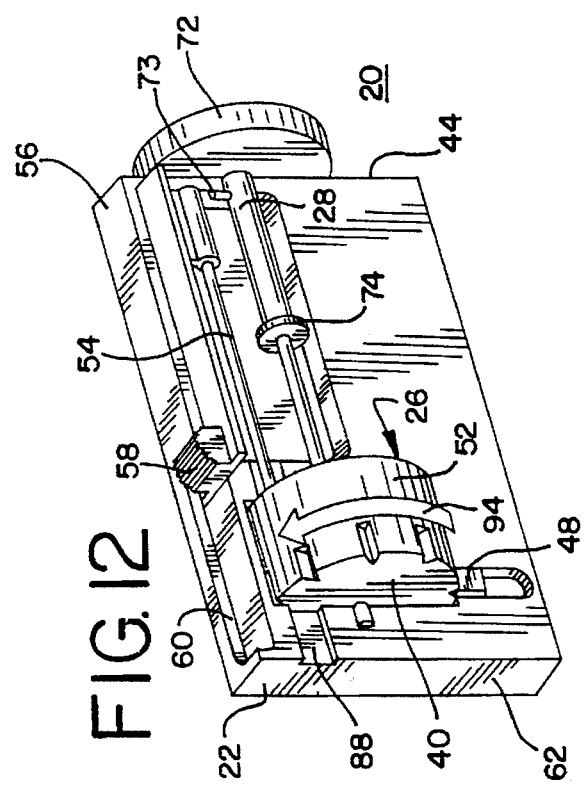

MEANS OF HANDLING MULTIPLE SENSORS IN A GLUCOSE MONITORING INSTRUMENT SYSTEM

This is a continuation, of application Ser. No. 08/423, 324, filed on Apr. 17, 1995, now abandoned.

BACKGROUND OF THE INVENTION

1. Field of the Invention

The present invention generally relates to a glucose monitoring system, and, more particularly, to a new and improved device for handling multiple sensors that are used in analyzing blood glucose.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end is adapted to be placed into the fluid being tested and has a capillary channel that extends in the sensor from the testing end to the reagent material. The testing end of the sensor can be placed into blood that has accumulated on a person's finger after the finger has been pricked. The fluid is absorbed into the capillary channel of the sensor by capillary action so that the sensor acts as a wick for the fluid being tested. The fluid then chemically reacts with the reagent material in the sensor so that an electrical signal indicative of the blood glucose level in the blood being tested is supplied to contacts projecting from the rear or contact end of the sensor. Alternatively, the results of the chemical reaction can be detected optically.

In order to couple the electrical signals produced at the sensor contacts to monitoring equipment, the sensors need to be inserted into sensor holders prior to the sensor end being placed into the fluid being tested. The holders have corresponding mating contacts that become coupled to the contacts on the sensor when the sensor is inserted into the holder. Consequently, the holders act as an interface between the sensor and monitoring equipment that accumulates and/ or analyzes the test results.

The sensors need to be maintained at an appropriate humidity level prior to being used so as to insure the integrity of the reagent materials in the sensor. Sensors can be packaged individually in tear-away packages so that they can be maintained at the proper humidity level. For instance, blister type packaging methods could be used. The packages can include desiccant material to maintain the proper humidity or desiccate level in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

SUMMARY OF THE INVENTION

Accordingly, an object of the present invention is to provide a new and improved device for handling multiple sensors used in testing blood glucose. Other objects of the present invention are to provide a new and improved blood glucose sensor handling device that enables a user to easily perform blood glucose testing; to provide a new and improved device for selectively placing one of a plurality of blood glucose sensors in position to be used for testing of a blood sample; to provide a new and improved blood glucose sensor handling device that contains a plurality of blood glucose sensors and that acts as an interface between the sensor and testing equipment when the sensor is being used; to provide a new and improved blood glucose sensor handling device that protects a plurality of sensors for use in testing of blood glucose from the environment in a desiccated condition until the sensor is to be used; and to provide a new and improved blood glucose sensor handling device that is adapted to receive a sensor magazine containing a plurality of blood glucose sensors so that individual ones of the sensors can be selectively placed in a sensing position when a sensor actuator on the handling device is moved to a sensing position.

In accordance with these and many other objects of the present invention, the present invention is embodied in a sensor dispensing instrument that is adapted to receive sensor magazines containing a plurality of blood glucose sensors. Each of the sensors has a generally flat, rectangular shape with a chamfered sensing end and an opposite contact end. The magazine may be in the form of a molded plastic right cylinder that contains a plurality of sensor slots that extend from a rear wall to a front wall. A series of detent grooves are disposed on the outer circumferential wall of the cylinder, each detent groove corresponding to one of the sensor slots. Each of the sensor slots is in fluid communication with a desiccant cavity and is adapted to receive therein one of the blood glucose sensors. The desiccant cavities are relatively shallow cavities for holding desiccant material. The desiccant material is placed in the cavity to insure that the corresponding sensor slot is maintained at an appropriate humidity or desiccate level so that the reagent material in the sensors will not be adversely affect prior to being used.

Prior to loading the sensors into the sensor slots, the front wall of the cylinder is covered with a front burst foil so as to seal the front end of each of the sensor slots. Thereafter, the sensors are loaded into the sensor slots and the desiccant material is disposed in the desiccant cavities. A rear burst foil is then placed over the rear wall so that the sensor slots and desiccant cavities are sealed by the front and rear burst foils.

The sensor instrument has an outer housing with a magazine opening extending laterally through the housing near a front or forward end of the housing. A pivot rod is retracted away from the front end of the instrument allowing the sensor magazine to be placed in the magazine opening. The pivot rod is moved forward through a central pivot opening in the sensor magazine and is locked into an operating position so that the sensor magazine is properly positioned in the magazine opening. The sensor magazine then needs to be manually rotated until a detent arm on the instrument housing extending into the magazine opening engages one of the detent grooves on the sensor magazine to insure that one of the sensor slots is in a sensor feeding position in alignment with a sensor push rod.

Once the sensor magazine is so positioned, a feed actuator near the top of the instrument housing is pushed forward resulting in the push rod piercing the rear burst foil and entering a sensor slot. The push rod continues to be moved forward until reaching a first detent or sensing position. As the push rod moves forward in the sensor slot, the push rod engages the contact end of the sensor and pushes the sensor out through the front burst foil and into a testing position. When in its testing position, contacts on the sensor mate with contacts in the instrument housing so that the sensor can be coupled through the instrument housing to sensor monitoring equipment. While in this position, the sensor end of the sensor can be placed in a blood sample that needs to be analyzed.

Once the test is completed, the push rod actuator is advanced forward further so that the push rod ejects the used sensor from the sensor handling instrument. Thereafter the push rod actuator and thereby the push rod are retracted to a standby position. After the push rod is in its standby position, the sensor magazine is rotated manually until the detent arm engages another detent groove so that another sensor slot is in alignment with the push rod. The sensor handling instrument then is in a condition for supplying another sensor to be used in a blood glucose test.

BRIEF DESCRIPTION OF THE DRAWING

The present invention, together with the above and other objects and advantages, can best be understood from the following detailed description of the embodiment of the invention illustrated in the drawing, wherein:

FIG. 1 is a perspective view of a blood glucose sensor handling instrument embodying the present invention shown with a sensor magazine ready for installation in the instrument;

FIG. 2 is a perspective view of a blood glucose sensor handling instrument of FIG. 1 shown with a sensor magazine installed in the instrument;

FIG. 3 is a rear plan view of the sensor magazine of FIG. 1 with the rear burst foil removed;

FIG. 4 is a front plan view of the sensor magazine of FIG. 1 with the front burst foil removed;

FIG. 5 is an exploded perspective view of the sensor magazine with the front and rear burst foils separated respectively from the front and rear walls of the sensor magazine;

FIG. 6 is side diagrammatic view of the sensor magazine showing how a pivot rod, push rod and a sensor are positioned relative to each other and the sensor magazine; and FIGS. 7–13 are diagrammatic views of the sensor handling instrument of FIG. 1 with a portion of the side of the instrument housing removed so that the operational sequence of use of the sensor handling instrument can be more readily depicted.

DETAILED DESCRIPTION OF THE PREFERRED EMBODIMENT

Referring now more specifically to FIGS. 1–2 of the drawings, therein is disclosed a blood glucose sensor handling or dispensing instrument generally designated by the reference numeral 20 and embodying the present invention. The sensor dispensing instrument 20 has an outer housing 22 with a magazine opening 24 extending laterally therethrough. The magazine opening 24 is adapted to receive a sensor magazine 26 so that it can be rotated on a pivot rod 28 that is extended through the sensor magazine 26. A series of ten sensor slots 30A–J (FIGS. 3–4) extend through the sensor magazine 26 from a rear wall 32 to a front wall 34. Desiccant cavities 36A–J (FIG. 3) respectively are associated with and in fluid communication with the sensor slots 30A–J. Sensors, such as the sensor 38 depicted in FIG. 6, are adapted to be disposed in each of the sensor slots 30A–J. The sensor slots 30A–J with the sensors 38 loaded therein are sealed by a front burst foil 40 that covers the front wall 34 of the sensor magazine 26 and a rear burst foil 42 that covers the rear wall 32 of the sensor magazine 26.

In order to load the sensor magazine 26 into the sensor instrument housing 22, the pivot rod 28 is retracted away from a rear wall 44 of the housing 22 and the sensor magazine 26 is positioned in the magazine opening 24. The pivot rod 28 then is moved forward through a central opening 46 in the sensor magazine 26 and is rotated until a detent arm 48 extending into the magazine opening 24 engages one of the detent grooves 50A–J on an outer periphery 52 of the magazine 26 (for example, the detent groove 50F depicted in FIG. 4).

With the sensor magazine 26 so disposed in the magazine opening 24, a sensor push or feed rod 54 disposed in the instrument housing 22 near a top wall 56 of the instrument housing 22 is in alignment with one of the sensor slots 30A–J (for example, the sensor slot 30A). When a push rod actuator 58 projecting through a slot 60 in the top wall 56 of the instrument housing 22 is pushed toward a front wall 62 of the instrument housing 22, the sensor push rod 54 pierces the rear burst foil 42 and enters the sensor slot 30A. As the sensor push rod 54 continues to be moved toward the front wall 62 of the housing 22, the sensor push rod 54 engages the sensor 38 disposed in the sensor slot 30A forcing the sensor 38 through the front burst foil 40 into a testing position. While in this testing position, the sensor 38 can be used in connection with analyzing a blood sample. The push rod 54 then can be moved further toward the front wall 62 of the housing 22 until the sensor 38 is ejected from the instrument 20. The push rod 54 thereafter is retracted toward the rear wall 44 of the housing 22 so that the sensor magazine 26 can be rotated to place another one of the sensor slots 30A–J in alignment with the push rod 54.

As is illustrated in FIGS. 3–5, the sensor magazine 26 has a generally right cylindrical shape and can be made of general purpose polypropylene material. One such type of suitable material is Exxon PD3345. The outer periphery 52 of the sensor magazine 26 includes the ten detent grooves 50A–J. Each of the grooves 50A–J extends a short distance from the front wall 34 of the sensor magazine 26 toward the rear wall 32. As is particularly shown in FIG. 4, each of the detent grooves 50A–J is disposed on the outer periphery 52 of the sensor magazine 26 diametrically opposite to a corresponding one of the sensor slots 30A–J. For example, the sensor slot 30A that is diametrically opposite the detent groove 50F will be in alignment with the push rod 54 when the detent arm 48 becomes lodged in the detent groove 50F.

Each of the sensor slots 30A–J extends completely through the sensor magazine 26 from the rear wall 32 to the front wall 34 and are generally rectangular in shape so that each of them is adapted to have disposed therein the sensor 38. The desiccant cavities 36A–J are respectively in fluid communication with the sensor slots 30A–J. The desiccant cavities 36A–J are of relatively shallow depth in that they extend only a short distance into the sensor magazine 26 from the rear wall 32 toward the front wall 34. The actual depth of the desiccant cavities 36A–J is determined by the space that is needed to accommodate a required amount of desiccant material that is to be disposed in each of the desiccant cavities 36A–J. The desiccant material that is disposed in the desiccant cavities 36A–J insures that the sensor slots 30A–J are maintained at an appropriate humidity level so that the reagent material in the sensor 38 disposed in the particular sensor slot 30A–J is not adversely affected prior to being used. The desiccant material might be in the form of a small bag or round bead of material or any other form that can be readily disposed in the desiccant cavities 36A–J. The amount of such desiccant material in the desiccant cavities 36A–J will be dependent on the amount that is required to maintain the sensor slots 30A–J in a desiccate state. One type of desiccant material that could be used is sold under the trademark NATRASORB and is available in powder, pellet and bead forms.

Each of the sensors 38 stored in the sensor magazine 26 is generally flat, rectangular in shape extending from a front or testing end 64 to a rear or contact end 66 (see FIG. 6). The front end 64 has oppositely extending chamfered edges 68 and 70 so that the front end 64 is adapted to puncture the front burst foil 40 when forced out of the sensor slots 30A–J by the push rod 54 and is adapted to be placed into the blood being analyzed. The contact end 66 has contacts (not shown) that are adapted to mate with contacts (not shown) in the instrument housing 22 when the sensor 38 is pushed into its testing position. In this manner, the sensor 38 can be coupled to monitoring equipment (not shown) which may be included in the instrument 20 or at a remote location. Consequently, the instrument 20 acts as an interface between such monitoring equipment and the sensors 38.

Each of the sensors 38 is provided with a capillary channel that extends from the front, testing end 64 of the sensor 38 to biosensing or reagent material disposed in the sensor 38. When the testing end 64 of the sensor 38 is placed into fluid, such as blood that is accumulated on a person's finger after the finger has been pricked, the fluid is absorbed into the capillary channel by capillary action so that the sensor 38 acts as a wick for the fluid being tested. The fluid then chemically reacts with the reagent material in the sensor 38 so that an electrical signal indicative of the blood glucose level in the blood being tested is supplied to the contacts at the contact end 66 of the sensor 38 and thereby through the instrument 20 to monitoring equipment. Alternatively, the results of the chemical reaction can be detected optically.

Prior to loading the sensors 38 into the sensor slots 30A–J, the front wall 34 of the sensor magazine 26 is covered with the front burst foil 40. The front burst foil 40 may be made of any material that will adequately seal the sensor slots 30A–J while providing a material that will burst or be pierced when the sensor 38 is pushed forward through the front wall 34 of the sensor magazine 26 by the push rod 54. One type of burst foil that can be used for both the front burst foil 40 and the rear burst foil 42 is AL-191-01 foil distributed by Alusuisse Flexible Packaging, Inc.

With the burst foil 40 in sealing relationship over the front wall 34 of the sensor magazine 26, the sensors 38 are loaded into the sensor slots 30A–J through the rear wall 32 of the sensor magazine 26. In addition, desiccant material is disposed in the desiccant cavities 36A–J. The rear burst foil 42 is secured over the rear wall 32 of the sensor magazine 26 such that the sensor slots 30A–J are sealed between the front burst foil 40 and the rear burst foil 42.

Once the front wall 34 and the rear wall 32 of the sensor magazine 26 are sealed, the sensor magazine 26 may be loaded into the housing 22. The procedure for loading the sensor magazine 26 into the housing 22 and the manner in which the sensor dispensing instrument 20 can be used are generally depicted in FIGS. 7–13. In particular, those figures disclose how the sensor magazine 26 is loaded into the sensor dispensing housing 22, how the sensors 38 contained in the sensor magazine 26 are placed into a testing position and thereafter ejected from the instrument 20, and finally, how the sensor magazine 26 is removed from the sensor dispensing housing 22 so that another sensor magazine 26 can be loaded into the magazine opening 24. In the diagrammatic drawings of FIGS. 7–13, a portion of the outer housing 22 has been removed in order to illustrate the operational sequence of use of the sensor dispensing instrument 20.

In order to load the sensor magazine 26 into the magazine opening 24, the pivot rod 28 has to be retracted so that it does not extend across or into the magazine opening 24. As is illustrated in FIG. 7, a circular or round knob 72 is attached to the rear end of the pivot rod 28. The knob 72 is rotated until a locking stub 73 extending from the pivot rod 28 is in alignment with a slot in the rear wall 44 of the housing 22. The pivot rod 28 then is retracted away from the magazine opening 24 by pulling on the knob 72 away from the rear wall 44 until a stop 74 associated with the pivot rod 28 engages the rear wall 44 of the housing 22. A spring mechanism (not shown) can be associated with the pivot rod 28 to propel the pivot rod 28 through the rear wall 44 of the housing 22 and away from the magazine opening 24 once the locking stub 73 has cleared the rear wall 44. With the pivot rod 28 so retracted, the sensor magazine 26 may be inserted into the magazine opening 24 as indicated by an arrow 76 in FIG. 7. The size of the distal portion 78 of the magazine opening 24. is slightly smaller than the portion of the magazine opening 24 through which the sensor magazine 26 is inserted so that the sensor magazine 26 cannot be accidentally pushed through the distal portion 78 of the magazine opening 24 as it is being loaded into the housing 22.

Once the sensor magazine 26 is disposed in the magazine opening 24, the knob 72 on the pivot rod 28 can be pushed toward the front wall 62 of the housing 22. As the pivot rod 28 is being moved toward the forward wall 62, the pivot rod 28 moves through the central opening 46 in the sensor magazine 26 and into a recess 80 at a forward edge 82 of the magazine opening 24. The locking stub 73 projecting from the pivot rod 28 will slide through an opening in the rear wall 44 and will lock the pivot rod 28 in the housing 22 after the pivot rod 28 is pushed forward as shown in FIG. 8.

The pivot rod 28 is configured (FIG. 6) so that it can be positioned in the central opening 46 of the sensor magazine 26 such that the sensor magazine 26 can be rotated or pivoted on the pivot rod 28. With the pivot rod 28 lodged in the central opening 46 of the sensor magazine 26, the sensor magazine 26 is manually rotated until the detent arm 48 projecting into the magazine opening 24 becomes lodged in one of the detent grooves 50A–J. For example, the detent arm 48 may be lodged in the detent groove 50F as is illustrated in FIG. 8 so that the sensor magazine 26 is in what can be termed a sensor feeding position.

The engagement of the detent arm 48 into the detent groove 50F insures that a corresponding sensor slot 30A is in alignment with the push rod 54. When a user of the sensor handling instrument 20 needs to use one of the sensors 38 to analyze a blood sample, the push rod actuator 58 that extends through the slot 60 in the top wall 56 of the housing 22 is pushed toward the front wall 62 of the housing 22 as indicated by an arrow 84 in FIG. 9. The push rod actuator 58 is connected to the push rod 54 such that the push rod 54 also is moved toward the front wall 62 of the housing 22. A forward end 86 of the push rod 54 is somewhat pointed so that as it is moved forward, it pierces the rear burst foil 42, enters into the sensor slot 30A, and engages the contact end 66 of the sensor 38 disposed in the sensor slot 30A. The continued movement of the push rod actuator 58 and thereby the push rod 54 in the direction of the arrow 84 results in the sensor 38 in the sensor slot 30A being thrust forward in the sensor slot 30A resulting in the front, chamfered end 64 of the sensor 38 piercing through the front burst foil 40.

The push rod actuator 58 is moved in the direction of the arrow 84 until it reaches a testing detent position as is illustrated in FIG. 9 of the drawings. When the push rod 54 has been advanced to this testing position, the sensor 38 is disposed in a groove 88 that extends from the front wall 62 to the forward edge 82 of the magazine opening 24. As is illustrated in FIG. 9, the sensor 38 extends out from the front wall 62 of the housing 22 when it is in this testing position so that the testing end 64 of the sensor 38 can be placed in the fluid being tested. Moreover, contacts near the contact end 66 of the sensor 38 engage or become mated with contacts in the groove 88 so that the electrical signals developed in the sensor 38 due to the absorption of fluid being tested can be transmitted to monitoring equipment.

Once the testing of the blood or other fluid is completed, the used sensor 38 that was in the sensor slot 30A needs to be ejected from the instrument 20. This is readily accomplished by moving the push rod actuator 58 further forward toward the front wall 62 in the direction of an arrow 90 in FIG. 10. As the push rod actuator 58 is moved in the direction of the arrow 90, the push rod 54 forces the used sensor 38 out of the groove 88 as is depicted in FIG. 10. The push rod actuator 58 is advanced until it is in the ejection position shown in FIG. 10 at which time the used sensor 38 becomes dislodged from the instrument 20.

In order to have the instrument 20 again be placed into a standby or ready condition so that another sensor 38 can be placed into a testing position, the push rod actuator 58 is returned to its standby condition by moving it in the direction of an arrow 92 in FIG. 11. As the push rod actuator 58 is returned to its standby position, the push rod 54 correspondingly is retracted out of the sensor slot 30A so that the sensor magazine 26 can be manually rotated in the direction indicated by an arrow 94 in FIG. 12. The sensor magazine 26 is rotated in this direction for a total of 36 degrees until the detent arm 48 becomes lodged in the next detent groove 50E on the periphery 52 of the sensor magazine 26 such that the next sensor slot 30J is in alignment with the push rod 54. The sensor 38 disposed in the sensor slot 30J can be dislodged from the sensor slot 30J for use in testing blood or the like in the same manner as the sensor 38 in the sensor slot 30A was placed in its testing position.

The above sequence of placing the sensor 38 disposed in the sensor slot 30A into a testing position and thereafter ejecting it from the instrument 20 can be repeated for each of the sensors disposed in the remaining sensor slots 30B–I until all of the sensors 38 in the sensor magazine 26 are used. Thereafter, the knob 72 can be retracted in the direction of an arrow 96 in FIG. 13 so that the sensor magazine 26 can be removed from the magazine opening 24 as indicated by the arrow 98 in FIG. 13 and a new sensor magazine 26 can be inserted into the magazine opening 24 as is illustrated in FIG. 7.

The sizes for the components of the sensor instrument 20 can vary depending on the particular use for which the instrument 20 is designed. In one configuration of the instrument 20, the outer diameter of the sensor magazine 26 is 1.210 inches (30.75 mm) and the depth of the sensor magazine 26 from the rear wall 32 to the front wall 34 is 0.670 inches (17.02 mm). When such a dimensional sensor magazine 26 is used, the sensors 38 can have a length dimension from the front end 64 to the contact 66 of 0.650 inches (16.51 mm), a width of 0.200 inches (5.08 mm), and a front dimension of 0.40 inches (10.16 mm) between the chamfered edges 68 and 70; the pivot rod 28 can have an outer thickness dimension of 0.125 (3.17 mm); and the push rod 54 can have an outer thickness dimension of 0.62 inches (1.57 mm). In such a specifically configured instrument 20, the push rod 54 may be positioned approximately 0.057 inches (1.46 mm) away from the rear wall 32 of the sensor magazine 26 when the instrument 20 is in its standby condition. The stroke of the push rod 54 to feed the sensor 38 from within one of the sensor slots 30A–J to its testing position would be approximately 0.752 inches (19.10 mm). In order to eject the sensor 38 from the housing 22, the further stroke of the push rod 54 would be approximately 0.282 inches (7.17 mm). When the sensor magazine 26 is to be loaded into or removed from the magazine opening 24, the pivot rod 28 is moved a stroke of approximately 0.797 inches (20.25 mm).

While the invention has been described with reference to details of the illustrated embodiment, these details are not intended to limit the scope of the invention as defined in the appended claims. For example, the instrument 20 can be used for testing fluids other than blood glucose. In fact, the instrument 20 can be used in connection with analyzing any type chemistry fluid that can be analyzed by means of a reagent material.

What is claimed and desired to be secured by Letters Patent of the United States is:

1. A sensor dispensing instrument (20) for handling of a plurality of fluid sensors (38) comprising:

a housing (22) having a magazine opening (24);

a sensor magazine (26) adapted to be disposed in said magazine opening (24), said sensor magazine (26) having a plurality of sensor slots (30A–J) each of which sensor slots (30A–J) is adapted to accommodate one of said plurality of fluid sensors (38);

a feed means (54);

a pivot means (28) for maintaining said sensor magazine (26) in said magazine opening (24) and permitting said sensor magazine (26) to be positioned so that one of said plurality of sensor slots (30A–J) is in alignment with said feed means (54); and feed actuator means (58) connected to said feed means (54) for advancing said feed means (54) through said sensor slot (30A–J) in alignment with said feed means (54) so that said sensor (38) in said sensor slot (30A–J) is placed into a testing position and for further advancing said feed means (54) so that said sensor (38) is ejected from said instrument (20).

2. A sensor dispensing instrument (20) as set forth in claim 1 wherein said sensor magazine (26) is a right cylinder having a plurality of detent means (50A–J) along its outer periphery (52), each of said detent means (50A–J) corresponding to one of said plurality of sensor slots (30A–J).

3. A sensor dispensing instrument (20) as set forth in claim 2 wherein said detent means (50A–J) and said sensor slots (30A–J) are equally spaced on said sensor magazine (26).

4. A sensor dispensing instrument (20) as set forth in claim 2 including a detent arm means (48) projecting into said magazine opening (24), one of said plurality of sensor slots (30A–J) being in alignment with said feed means (54) when said detent arm means (48) is disposed in one of said plurality of detent means (50A–J).

5. A sensor dispensing instrument (20) as set forth in claim 1 wherein said sensor magazine (26) includes a plurality of desiccant cavities (36A–J), each of which desiccant cavities (36A–J) is in fluid communication with one of said plurality of sensor slots (30A–J).

6. A sensor dispensing instrument (20) as set forth in claim 5 including desiccant material in each of said plurality of desiccant cavities (36A–J) so that each of said plurality of sensor slots (30A–J) is maintained in a desiccate state.

7. A sensor dispensing instrument (20) as set forth in claim 5 wherein said sensor magazine (26) includes first and second walls (32, 34) with each of said plurality of desiccant cavities (36A–J) extending from said first wall (32) toward said second wall (34) and including first foil means (42) covering said first wall (32) such that said plurality of desiccant cavities (36A–J) are sealed by said first foil means (42).

8. A sensor dispensing instrument (20) as set forth in claim 1 wherein said sensor magazine (26) includes first and second walls (32, 34) with each of said plurality of sensor slots (30A–J) extending from said first wall (32) to said second wall (34) and including first foil means (42) covering said first wall (32) and a second foil means (40) covering said second wall (34) such that said plurality of sensor slots (30A–J) are sealed between said first and second foil means (42, 40).

9. A sensor dispensing instrument (20) as set forth in claim 8 wherein as said feed means (54) is being advanced by said feed actuator means (58) said feed means (54) pierces said first foil means (42), enters into said sensor slot (30A–J) in alignment with said feed means (54) and engages said sensor (38) in said sensor slot (30A–J) forcing said sensor (38) to pierce through said second foil means (40) into said testing position.

10. A sensor dispensing instrument (20) as set forth in claim 9 wherein each of said plurality of sensors (38) includes a chamfered testing end (64) that is adapted to pierce said second foil means (40) and that is adapted to be placed in fluid to be tested.

11. A sensor dispensing instrument (20) as set forth in claim 1 wherein said feed actuator means (58) returns said feed means (54) to a standby position after said one said plurality of sensors (38) is ejected from said instrument (20).

12. A sensor dispensing instrument (20) as set forth in claim 1 wherein said pivot means (28) has a first position wherein said sensor magazine (26) is permitted to rotate on said pivot means (28) and a second position retracted away from said magazine opening (24) so that said sensor magazine (26) can be inserted into or removed from said magazine opening (24).

13. A sensor dispensing instrument (20) as set forth in claim 12 including a knob means (72) associated with said pivot means (28) for moving said pivot means (28) to said first and second positions.

14. A sensor dispensing instrument (20) for handling of a plurality of fluid sensors (38) comprising:

a housing (22) having a magazine receiving means (24);

a sensor magazine (26) adapted to be disposed in said magazine receiving means (24) and having first and second walls (32, 34), said sensor magazine (26) having a plurality of sensor slots (30A–J) extending between said first and second walls (32, 34) with one of said plurality of fluid sensors (38) being disposed in each of said sensor slots (30A–J) and a plurality of desiccant cavities (36A–J) extending from said first wall (32) towards said second wall (34), each of which desiccant cavities (36A–J) having desiccant material disposed therein and being in fluid communication with one of said sensor slots (30A–J);

a push rod (54);

a pivot means (28) engageable with said sensor magazine (26) when said sensor magazine (26) is positioned in said magazine receiving means (24) for positioning said sensor magazine (26) and permitting the rotation of said sensor magazine (26) so that one of said plurality of sensor slots (30A–J) is in alignment with said push rod (54); and first foil means (42) covering said first wall (32) and a second foil means (40) covering said second wall (34) such that said plurality of sensor slots (30A–J) and said plurality of desiccant cavities (36A–J) are sealed by said first and second foil means (42, 40); and actuator means (58) associated with said push rod (54) for advancing said push rod (54) through said first foil means (42) into said sensor slot (30A–J) in alignment with said push rod (54) so that said sensor (38) in said sensor slot (30A–J) is forced through said second foil means (40) and placed into a testing position and for further advancing said push rod (54) so that said sensor (38) is ejected from said instrument (20).

15. A sensor dispensing instrument (20) as set forth in claim 14 including a detent arm means (48) projecting into said magazine receiving means (24) and wherein said sensor magazine (26) has a plurality of detent means (50A–J) along its outer periphery (52), each of said detent means (50A–J) corresponding to one of said plurality of sensor slots (30A–J) so that one of said plurality of sensor slots (30A–J) is in alignment with said push rod (54) when said detent arm means (48) is disposed in one of said plurality of detent means (50A–J).

16. A sensor magazine (26) for use in a dispensing instrument (20) for fluid sensors (38) comprising:

a sensor housing portion (22) having first and second walls (32, 34) with a plurality of sensor slots (30A–J) extending between said first and second walls (32, 34), each of said plurality of said sensor slots (30A–J) being adapted to receive a fluid sensor (38); and first foil means (42) covering said first wall (32) and a second foil means (40) covering said second wall (34) such that said plurality of sensor slots (30A–J) are sealed by said first and second foil means (42, 40).

17. A sensor magazine (26) as set forth in claim 16 including a plurality of desiccant cavities (36A–J) extending from said first wall (32) towards said second wall (34), each of which desiccant cavities (36A–J) having desiccant material disposed therein and being in fluid communication with one of said sensor slots (30A–J).

18. A sensor magazine (26) as set forth in claim 17 wherein said first foil means (42) additionally seals said plurality of desiccant cavities (36A–J).

19. A sensor magazine (26) as set forth in claim 16 wherein said dispensing instrument (20) includes a feed means (54) that is adapted to pierce said first foil means (42), enter into one of said sensor slots (30A–J) and engage said sensor (38) in said sensor slot (30A–J) forcing said sensor (38) to pierce through said second foil means (40) into a testing position.

20. A sensor magazine (26) as set forth in claim 19 wherein said said first and second foil means (42, 40) are in planes generally transverse to the direction in which said sensor (38) is forced as said sensor (38) pierces said second foil means (40).

21. A method of handling a plurality of fluid sensors (38) comprising:

installing a sensor magazine (26) into a magazine opening (24) in a housing (22) of a sensor dispensing instrument (20), said sensor magazine (26) having a plurality of sensor slots (30A–J), each of which sensor slots (30A–J) is adapted to accommodate one of said plurality of fluid sensors (38);

pivoting said sensor magazine (26) so that one of said plurality of sensor slots (30A–J) is in alignment with said feed means (54);

actuating a feed actuator means (58) to advance a feed means (54) through said sensor slot (30A–J) in alignment with said feed means (54) so that said sensor (38) in said sensor slot (30A–J) is placed into a testing position; and further actuating said feed actuator means (58) so that said feed means (54) is further advanced to eject said sensor from said instrument (20).

22. A method of handling a plurality of fluid sensors (38) as set forth in claim 21 wherein said sensor magazine (26) includes first and second walls (32, 34) with each of said plurality of sensor slots (30A–J) extending from said first wall (32) to said second wall (34) and including first foil means (42) covering said first wall (32) and a second foil means (40) covering said second wall (34) such that said plurality of sensor slots (30A–J) are sealed between said first and second foil means (42, 40) and wherein said feed means (54) pierces said first foil means (42) as said feed means (54) is advanced into said sensor slot (30A–J) and said sensor (38) pierces said second foil means (40) as said feed means (54) advances said sensor (38) into said testing position.

23. A method of handling a plurality of fluid sensors (38) as set forth in claim 21 wherein said sensor magazine (26) is pivoted until a detent arm (48) extending into said magazine opening (24) becomes lodged in one of plurality of latch grooves (50A–J) in an outer periphery (52) of said sensor magazine (26), each of which latch grooves (50A–J) corresponds to one of said sensor slots (30A–J).

* * * * *